(12) United States Patent
Chen

(10) Patent No.: US 12,303,188 B2
(45) Date of Patent: May 20, 2025

(54) ELECTRIC PULSE ABLATION DEVICE AND SIMULATION METHOD APPLICABLE TO THE SAME

(71) Applicant: Hangzhou Ready Biological Technology Co., Ltd, Zhejiang (CN)

(72) Inventor: Yonggang Chen, Zhejiang (CN)

(73) Assignee: HANGZHOU READY BIOLOGICAL TECHNOLOGY CO., LTD, Zhejiang (CN)

( * ) Notice: Subject to any disclaimer, the term of this patent is extended or adjusted under 35 U.S.C. 154(b) by 903 days.

(21) Appl. No.: 17/600,514

(22) PCT Filed: Oct. 16, 2019

(86) PCT No.: PCT/CN2019/111454
§ 371 (c)(1),
(2) Date: Sep. 30, 2021

(87) PCT Pub. No.: WO2021/022673
PCT Pub. Date: Feb. 11, 2021

(65) Prior Publication Data
US 2022/0202477 A1  Jun. 30, 2022

(30) Foreign Application Priority Data
Aug. 7, 2019  (CN) .......................... 201910724331.2

(51) Int. Cl.
*A61B 18/14*  (2006.01)
*A61B 8/00*  (2006.01)
(Continued)

(52) U.S. Cl.
CPC .......... *A61B 18/1477* (2013.01); *A61B 90/50* (2016.02); *A61B 8/4209* (2013.01);
(Continued)

(58) Field of Classification Search
CPC .................................................... A61B 90/11
See application file for complete search history.

(56) References Cited

U.S. PATENT DOCUMENTS

2009/0076502 A1* 3/2009 Azure ................ A61B 18/1477
606/41
2018/0206926 A1* 7/2018 Kitamura ............... A61B 34/30

FOREIGN PATENT DOCUMENTS

| CN | 104248471 A | 12/2014 |
|---|---|---|
| CN | 105208957 A | 12/2015 |

(Continued)

*Primary Examiner* — Ronald Hupczey, Jr.
(74) *Attorney, Agent, or Firm* — Muncy, Geissler, Olds & Lowe, P.C.

(57) ABSTRACT

An electric pulse ablation device and a simulation method applicable to the same belong to the technical field of electric pulse devices. A pressure sensor module can realize the early warning of a puncture process, thus avoiding damage of normal organ tissues; and a positioning system can realize positioning navigation of tumor operation puncture. In the present application, according to the changes of the electrolyte parameters collected by a biological impedance analyzer, an impedance adaptation module adjusts input pulse parameters in time, and keeps adaptive high voltage and steep pulse to achieve the best tumor destruction effect; and the ablation effect is very ideal.

4 Claims, 11 Drawing Sheets

(51) Int. Cl.
  *A61B 18/00*   (2006.01)
  *A61B 90/50*   (2016.01)
(52) U.S. Cl.
  CPC ............... *A61B 2018/00577* (2013.01); *A61B 2018/00642* (2013.01); *A61B 2018/00702* (2013.01); *A61B 2018/00773* (2013.01); *A61B 2018/00875* (2013.01)

(56) References Cited

FOREIGN PATENT DOCUMENTS

| CN | 106725526 A | 5/2017 |
| CN | 107432765 A | 12/2017 |
| CN | 109157280 A | 1/2019 |
| WO | WO-2013165714 A1 | 11/2013 |

* cited by examiner a  Pre-puncture state          b  Post-puncture state

Boundary conditions meet requirements and results converge.

ELECTRIC PULSE ABLATION DEVICE AND SIMULATION METHOD APPLICABLE TO THE SAME

TECHNICAL FIELD

The present application relates to an electric pulse ablation device and a simulation method applicable to the same, belonging to the technical field of electric pulse devices.

BACKGROUND ART

Nanosecond pulse tumor therapy is a non-thermal/cold ablation technology, which uses high-pressure nanosecond pulses to act on the internal structure of tumor cells, causing functional changes in cells, and inducing natural apoptosis through cell membrane perforation; while inducing tumor apoptosis, it will not cause thermal damage to surrounding normal tissues or blood vessels, neurovascular bundles, urethra, rectum, nerves, etc.

However, the existing ablation device has the following defects:

First, for the existing electric pulse ablation device, in the process of surgical puncture, the puncture force is difficult to control, so it is usually easy to puncture or damage the key tissues or membrane walls.

Second, in the process of the existing electric pulse ablation, due to the impedance of the tumor tissues, the electrolyte parameters of the tissue seeping fluid in the ablation region change with the ablation time, and the changing electrolyte parameters are not matched with the initial electric pulse ablation parameters anymore, resulting in that the ablation effect is poor.

Further, the setting of the pulse parameters, the spacing between double needle electrodes, the length of the electrode working part and other parameters of the electric pulse ablation device will influence the range of the electric field covering the tumor and the field intensity distribution during high-voltage nanosecond pulse therapy, and then influence the treatment effect of pulse ablation.

Since the tumor varies from person to person, the position of the tumor is changeable, the shape and size of the tumor are different, and doctors need to set pulse parameters, the spacing between the double needle electrodes, the length of the electrode working part and other parameters, it is difficult to set reasonable and effective parameters depending on doctors' own experience; even experienced doctors need to spend a lot of time to debug and demonstrate, it is time-consuming and laborious, and it is difficult to ensure that the settings are reasonable and effective every time.

SUMMARY

Aiming at the defects of the prior art, one purpose of the present application is to provide an electric pulse ablation device, which can realize the early warning of a puncture process through a pressure sensor module, avoid damage of normal organ tissues; can realize positioning navigation of tumor operation puncture; can adjust the pulse parameters of the pulse generated by a pulse generator through an impedance adaptation module, such that the ablation effect is very ideal.

Another purpose of the present application is to provide an electric pulse ablation simulation method which can, by establishing a simulation database, perform simulation according to tumors to obtain parameter setting values of the ablation device as setting bases for selection by doctors, can effectively decrease the burden of the doctors, and is time-saving and labor-saving.

In order to achieve the purposes, the present application adopts the following technical solution:

An electric pulse ablation device includes a pulse generator, a positioning system, a needle feeding mechanism, a sensor module, a biological impedance analyzer, and an impedance adaptation system;

the pulse generator is configured to generate an electric pulse;

the positioning system is configured to read the size and position of tissues;

the needle feeding mechanism is provided with a puncture guide needle;

the sensor motor is configured to sensor puncture pressure;

the biological impedance analyzer is configured to monitor the impedance of tissues to be detected in real time;

the impedance adaptation system is configured to adjust the pulse parameters of the pulse generated by the pulse generator.

Due to the difference in characteristic density, viscoelasticity, tension and pressure resistance of tissues, the puncture force at different tissue layers is different. In the puncture process of the puncture guide needle, when the puncture force reaches a first critical value Fc1, the puncture force drops sharply, indicating that the needle pierces a first layer of tissues; when the puncture force reaches Fc2, the puncture guide needle begins to enter a second layer of tissues. Therefore, in the present application, a sensor module is provided for sensing the puncture pressure, which can judge which tissue and depth the puncture needle punctures section by section, and judge whether the puncture is correct in real time.

When the tumor is ablated, the impedance of the tumor tissues changes with the ablation time in the ablation process. Therefore, in the present application, a biological impedance analyzer is provided for monitoring the impedance of the tissues to be detected in real time; according to the change of the tissue conductivity, the impedance adaptation system instructs the pulse generator to automatically match the electric pulse parameters.

In the present application, the pressure sensor module can realize the early warning of a puncture process, thus avoiding damage of normal organ tissues; and the positioning system can realize positioning navigation of tumor operation puncture.

In the present application, according to the changes of the electrolyte parameters collected by the biological impedance analyzer, the impedance adaptation module adjusts the input pulse parameters in time, and keeps adaptive high voltage and steep pulse to achieve the best tumor destruction effect; and the ablation effect is very ideal.

As an alternative technical measure, the needle feeding mechanism includes a base, a puncture needle tube seat, a support frame, a front sealing piston, a rear sealing piston, an electrode crimping socket, an air injection pump, an indicator lamp, a pin tumbler lock, a front air vent, a rear air vent, a puncture needle pressure chamber, a front air injection tube, a front emptying switch, an electrode pressure chamber, a rear emptying switch, a rear air injection tube, and an electrode.

The puncture force of each tissue is different. When the puncture needle enters different tissues, an AI system collects the pressure value detected by the pressure sensor to determine whether the pressure change is within an allowable range. If it exceeds the pressure range, the color of the indicator lamp in the normal state changes to flashing or highlighting, and the puncture is stopped to remind a doctor to check the type-B ultrasound images to determine to continue the puncture or exit and start again.

In the present application, the scheme of the needle feeding mechanism is detailed, ingenious and practical.

As an alternative technical measure, the positioning system includes an orientation device, a transverse support rod, a lifting connecting rod, lifting platforms, a lifting rocker, a longitudinal support rod, a fixed locking block, a longitudinal rod locking handle, a fixing frame locking handle, a lifting pressing block, a lifting locking handle, and a lifting fixing block; the scheme is detailed and practical.

The fixed locking block sleeves a sickbed guide groove and the position is locked through the longitudinal rod locking handle; the longitudinal support rod is mounted on the fixed locking block, the position is locked through the fixing frame locking handle, and the distance is capable of being roughly adjusted according to the position of a human body; the lifting platforms are fixed on the longitudinal support rod, the lifting connecting rod between the two lifting platforms is connected to make the lifting synchronous, and the lifting rocker is mounted on the lifting platform on one side; the lifting fixing block is provided on the lifting platform, the transverse support rod is disposed in a lifting fixing block clamping slot, a hinge structure is provided between the lifting pressing block and the lifting fixing block, and the lifting locking handle fixedly locks the transverse support rod.

As an alternative technical measure, the orientation device includes an orientation plate, an ultrasonic probe, a probe fixing strip, a probe fixing frame, a probe adjusting handle, a positioning frame rear plate, a positioning frame locking handle, a positioning frame fixing plate, a positioning frame, a probe locking screw, an orientation plate frame locking screw, an orientation plate fixing frame, an orientation plate locking screw, a synchronous belt pulley I and a synchronous belt pulley II.

The orientation device is fixed on the transverse support rod through a clamping slot in the positioning frame fixing plate, and the position is capable of being adjusted on the left and right of the transverse support rod and is capable of being locked through the positioning frame locking handle; after the patient is in place on the sickbed, the height of the lifting platforms is adjusted through the lifting rocker, and the left and right positions of the orientation device are adjusted through the positioning frame fixing plate, such that the ultrasonic probe is aligned with the patient's anus; the positioning frame is provided on the positioning frame fixing plate, the probe fixing frame is provided at an upper end of the positioning frame, the ultrasonic probe is fixed in a groove in the probe fixing frame, and the position is locked through the probe locking screw through the probe fixing strip; the orientation plate fixing frame is provided at a front end of the positioning frame, and the position is locked through the orientation plate frame locking screw; the orientation plate is provided on the orientation plate fixing frame, and the position is locked through the orientation plate locking screw; the inside of the positioning frame is hollow and is provided with the synchronous belt pulley I and the synchronous belt pulley II, the probe fixing frame is fixed on the synchronous belt pulley I, the positioning frame rear plate is provided at a rear end of the positioning frame, the probe adjusting handle is provided on the positioning frame rear plate, the probe adjusting handle is fixed coaxially with the synchronous belt pulley II, and the ultrasonic probe is capable of moving forward or backward through the probe adjusting handle.

As an alternative technical measure, the sensor module group includes a pressure sensor module and a depth sensor.

A simulation method applicable to an electric pulse ablation device includes establishing a simulation database, which specifically includes the following steps:

step 1: collecting tumor image data, establishing a database, and marking accurate regions of tumors in tissues;

step 2: according to the tissue parameters, the spacing between different double needle electrodes and the length of an electrode working part, establishing a parameter 3D model;

step 3: realizing the variation of the spacing and the length through the parameter 3D model, simulating different pulse amplitudes, pulse widths, pulse frequencies and feed modes, performing simulation based on different parameter 3D models, and selecting and adding parameter settings with large electric field coverage range and uniform field intensity distribution into the simulation database.

The present application can, by establishing a simulation database, perform simulation according to tumors to obtain parameter setting values of the ablation device as setting bases for selection by doctors, can effectively decrease the burden of the doctors, and is time-saving and labor-saving. In addition, the parameters set at each time are not influenced by the external world, and thus the reasonableness and effectiveness of the parameter settings are effectively kept.

As an alternative technical means, in step 1, a full-automatic segmentation model of tissues and tumors is designed by using a convolutional neural network based on a DenseNet network model; then learning is performed by using marked original images in the database and a tumor mask of the same group as inputs of a convolutional network;

in step 2, the tissue parameters are tissue dielectric constant, relative permeability, bulk conductivity and dielectric loss tangent.

As an alternative technical means, the impedance of tumor tissues changes with ablation time in the process of tumor ablation, so for the simulation method provided by the present application, for the sake of ablation effectiveness, it is necessary to simulate the change of tissue conductivity in the ablation process, adjust an external ablation electric field according to the change of tissue conductivity, and then adjust the pulse parameters;

a change model of the tissue conductivity and the external ablation electric field is established, and the intensity of the external ablation electric field is calculated according to the change of the tissue conductivity; a functional relationship between the tissue conductivity and the external ablation electric field is as follow:

$$\sigma=\sigma_0(1+\alpha(T-T_0))+(\sigma'-\sigma_0)F_{flc}(E-E_1,E_{range})$$

where $T=T_0$ all the time since the temperature of a pulse electric field does not change or changes very slightly;

$\sigma_0$ is the initial conductivity of tissues, and the initial conductivity of normal tissues and tumors are capable of being measured through a test circuit;

$\sigma'$ is the conductivity of tissues only in an electric field, and the conductivity of normal tissues and tumors is capable of being measured through a test circuit;

$F_{flc}$ is a smooth Heaviside function with second-order continuous derivatives;

E is the intensity of the electric field;

the values of $E_1$ and $E_{range}$ are respectively 30 KV/cm−X and 30 kV/cm+X, where X is a voltage threshold, so as to ensure that the conductivity changes with the intensity of the electric field within a range of the intensity threshold of the electric field forming functional changes in cells;

α is a calculation coefficient;

in the process of electric pulse ablation, the impedance of the tumor tissues and the electrolyte parameters of the tissue seeping fluid in the ablation region change with the ablation time, and the changing electrolyte parameters are not matched with the initial electric pulse ablation parameters anymore, resulting in that the ablation effect is poor; therefore, in order to ensure that the reasonable pulse parameters can be set and the change of electrolyte parameters can be understood in real time, the input pulse parameters are adjusted in time to keep adaptive high voltage and steep pulse to achieve the best tumor destruction effect;

the conductivity and the impedance Z are mutually reciprocals;

the tissue impedance change calculation formula is as follow: $Z=R_e//(Z_C+R_i)$ where $Z_C=1/(2\pi fC)$, where $R_i$, $R_e$ and C are respectively equivalent to intracellular fluid resistance, extracellular fluid resistance and cell membrane capacitance, and f represents current frequency. According to the initial impedance of the tissues, the initial conductivity of the tissues can be calculated, so as to facilitate formula application.

As an alternative technical measure, a finite-element simulation algorithm based on a discontinuous Galerkin time domain algorithm is used to establish the model, and the electric field distribution in tumors and normal tissues is obtained by solving the following equation:

$$\nabla \times \left(\frac{1}{\mu_r}\nabla \times E\right) - k_o^2\epsilon_r E = 0$$

where ∇ is curl symbol; $\mu_r$ is the relative permeability of a medium; $\epsilon_r$ is the relative conductivity of the medium; k is Coulomb constant; E is the intensity of the electric field;

through the above formula, the intensity of the electric field of the tissues under a normal state can be obtained, so as to determine more reasonable initial pulse parameters;

in order to obtain the optimal pulse parameters and electrode placement for different shapes and sizes of tumors, a grid initialization algorithm and an optimized iterative adaptation algorithm are used to optimize the pulse parameters and electrode parameters; grids are coupled by numerical flux and are automatically refined and subdivided, convergence is achieved after several iterations, and the electric field distribution in the solution region meets characteristics of a physical environment and boundary conditions.

As an alternative technical measure, the simulation method applicable to the electric pulse ablation device further includes step 5 of analyzing a solid tumor and giving setting schemes: taking ultrasonic images of a patient, performing analysis to form a tumor tissue 3D model, selecting suitable application data in the simulation database, and simulating the placement of a single group or a plurality of groups of electrodes according to the size and morphology of the tumor to form varied pulse setting schemes as setting bases for selection by doctors. The time of the doctors is saved, and the reasonableness and effectiveness of parameter settings are improved.

Compared with the prior art, the present application has the following beneficial effects:

In the present application, the pressure sensor module can realize the early warning of a puncture process, thus avoiding damage of normal organ tissues; and the positioning system can realize positioning navigation of tumor operation puncture.

In the present application, according to the changes of the electrolyte parameters collected by the biological impedance analyzer, the impedance adaptation module adjusts the input pulse parameters in time, and keeps adaptive high voltage and steep pulse to achieve the best tumor destruction effect; and the ablation effect is very ideal.

Further, the present application can, by establishing a simulation database, perform simulation according to tumors to obtain parameter setting values of the ablation device as setting bases for selection by doctors, can effectively decrease the burden of the doctors, and is time-saving and labor-saving. In addition, the parameters set at each time are not influenced by the external world, and thus the reasonableness and effectiveness of the parameter settings are effectively kept.

DESCRIPTION OF REFERENCE SIGNS

Figure 1:
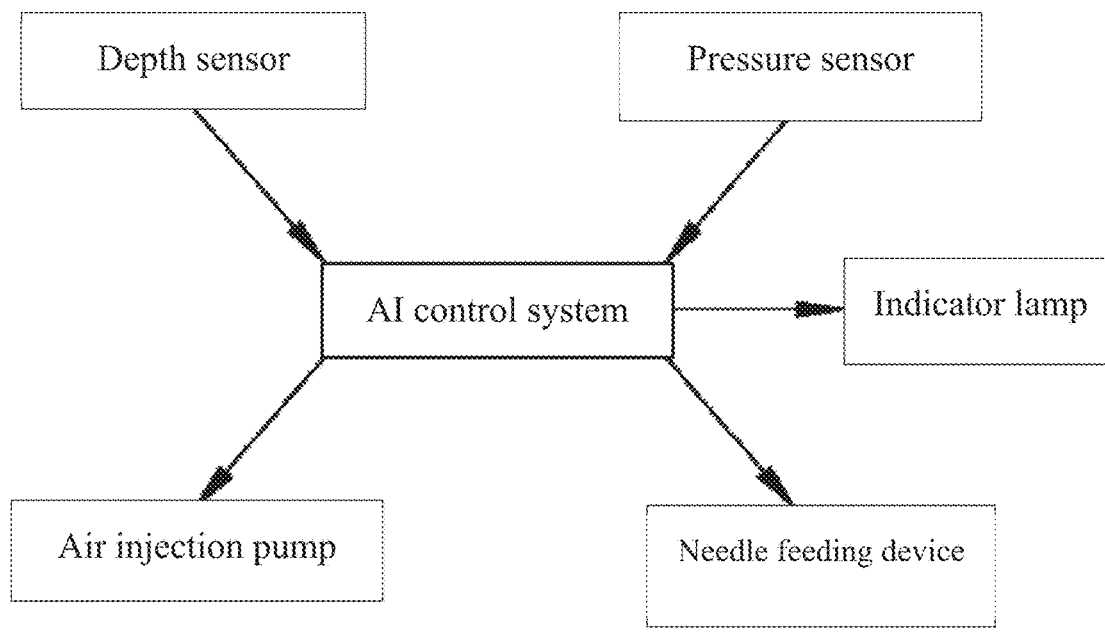
FIG. 1 illustrates a control flowchart according to the present application.

1—puncture guide needle; 2—base; 3—puncture needle tube seat; 4—support frame; 5—front sealing piston;

6—rear sealing piston; 7—electrode crimping socket; 8—AI control system; 9—air injection pump; 10—indicator lamp; 11—puncture depth sensor; 12—pressure sensor; 13—pin tumbler lock; 14—front air vent; 15—rear air vent; 16—puncture needle pressure chamber; 17—front air injection tube; 18—front emptying switch; 19—electrode pressure chamber; 20—rear emptying switch; 21—rear air injection tube; 22—electrode;

201—orientation device; 202—transverse support rod; 203—lifting connecting rod; 204—lifting platform; 205—lifting rocker; 206—longitudinal support rod; 207—fixed locking block; 208—longitudinal rod locking handle; 209—fixing frame locking handle; 2010—lifting pressing block; 2011—lifting locking handle; 2012—lifting fixing block;

3011—orientation plate; 3012—ultrasonic probe; 3013—probe fixing strip; 3014—probe fixing frame; 3015—probe adjusting handle; 3016—positioning frame rear plate; 3017—positioning frame locking handle; 3018—positioning frame fixing plate; 3019—positioning frame; 30110—probe locking screw; 30111—orientation plate frame locking screw; 30112—orientation plate fixing frame; 30113—orientation plate locking screw; 30114—synchronous belt pulley I; 30115—synchronous belt pulley II.

DESCRIPTION OF THE EMBODIMENTS

In order to make the purposes, technical solutions and advantages of the present application clearer, the present application will be further described below in detail in combination with the embodiments with reference to the drawings. It should be understood that the specific embodiments described herein are only used for explaining the present application instead of limiting the present application.

On the contrary, the present application covers any replacement, modification, equivalent method and solution defined by the claims in terms of the essence and scope of the present application. Further, in order to make the public better understand the present application, some specific details are described in detail in the detailed description of the present application below. It is also possible to fully understand the present application without description of these details for those skilled in the art.

It should be noted that when two components are called "fixedly connected", the two components may be directly connected or there may be an intermediate component. On the contrary, when one component is called "directly on" another component, there is no intermediate component. The terms "above", "below" and similar expressions used herein are only used for the purpose of description.

Unless otherwise defined, all technical and scientific terms used herein have the same meanings as those commonly understood by those skilled in the art of the present application. The terms used herein are used for the purpose of describing the specific embodiments only and are not intended to limit the present application. The term "or/and" used herein includes any or all combinations of one or more relevant listed items.

An electric pulse ablation device includes a pulse generator, a positioning system, a needle feeding mechanism, a sensor module, a biological impedance analyzer, and an impedance adaptation system;

the pulse generator is configured to generate an electric pulse;

the positioning system is configured to read the size and position of tissues;

the needle feeding mechanism is provided with a puncture guide needle;

the sensor module is configured to sensor puncture pressure;

the biological impedance analyzer is configured to monitor the impedance of tissues to be detected in real time;

the impedance adaptive system is configured to adjust the pulse parameters of the pulse generated by the pulse generator.

Figure 2:
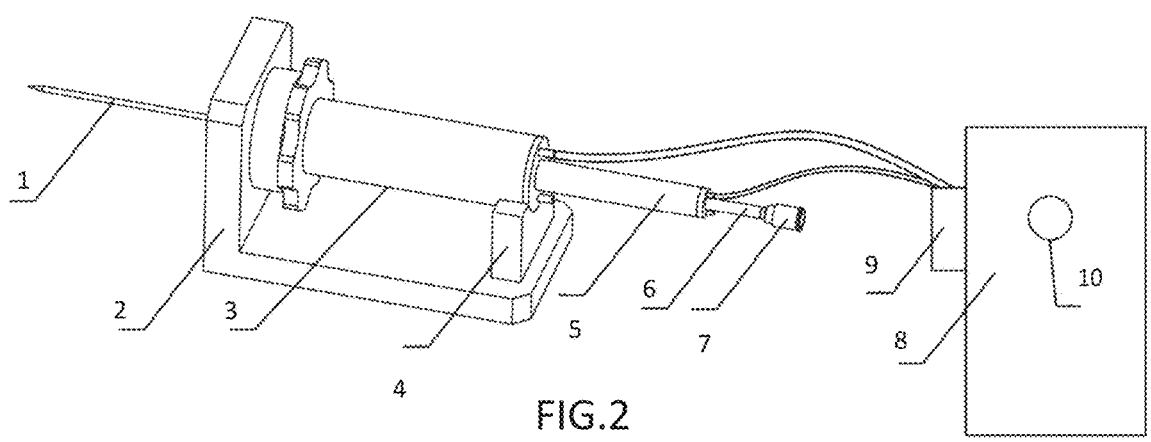
FIG. 2 illustrates a schematic view of a structure according to the present application.
Figure 3:
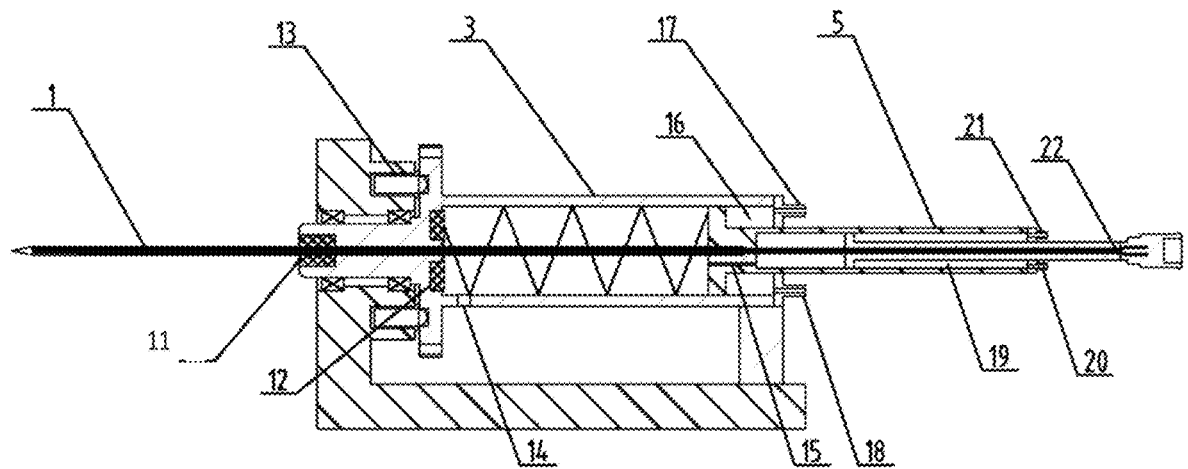
FIG. 3 illustrates a sectional view of the structure illustrated in FIG. 2.

Referring to FIGS. 1-3, a specific embodiment of the needle feeding mechanism of the present application is as follows:

The working principle of the needle feeding mechanism is as follows: taking the treatment of a prostate tumor as an example, a puncture needle enters the tumor through perineal skin, cavity, prostate tissue envelope, prostate tissues, tumor envelope and tumor tissues, and the puncture force of each tissue is different. When the puncture needle enters different tissues, an AI system collects the pressure value detected by a pressure sensor 12, and determines whether the pressure change is within an allowable range; if it exceeds the pressure range, the color of the lamp in the normal state changes to flashing or highlighting, and the puncture is stopped to remind a doctor to check the type-B ultrasound images to determine to continue the puncture or exit and start again.

The needle feeding system mainly includes a puncture guide needle 1, a base 2, a puncture needle tube seat 3, a support frame 4, a front sealing piston 5, a rear sealing piston 6, an electrode 22 crimping socket 7, an AI control system 8, an air injection pump 9, an indicator lamp 10, a puncture depth sensor 11, a pressure sensor 12, a pin tumbler lock 13, a front air vent 14, a rear air vent 15, a puncture needle pressure chamber 16, a front air injection tube 17, a front emptying switch 18, an electrode 22 pressure chamber 19, a rear emptying switch 20, a rear air injection tube 21, and an electrode 22.

A specific embodiment of automatic control of needle feeding of the present application is as follows:

The AI control system 8 sets the standard pressure of puncturing different tissues and the pressure range for determination; makes the front sealing piston 5 and the rear sealing piston 6 in the initial positions, and turns off the front emptying switch 18 and the rear emptying switch 20; adjusts the position and direction of the base 2 such that the puncture guide needle 1 is aligned with the tumor and the needle tip contacts the perineal skin surface. The AI control system 8 controls the air injection pump 9 to inject air into the puncture needle pressure chamber 16 according to the set standard pressure to push the puncture guide needle 1 into the human body. The pressure sensor 12 transmits the collected pressure information in the puncture needle pressure chamber 16 to the AI control system 8, and air is injected when the real-time pressure is less than the set standard puncture pressure to increase the air pressure in the pressure chamber and reach the standard puncture pressure set for puncture. The puncture depth sensor 11 transmits the collected puncture depth value to the AI control system 8. The AI control system 8 determines the position of tissues at which the puncture needle is located according to the puncture pressure and the puncture depth, and adjusts the puncture pressure. After the puncture guide needle 1 reaches the set position, the AI control system 8 controls to close the front air injection tube 17, maintains the pressure in the puncture needle pressure chamber 16, and locks the position of the puncture guide needle 1. The AI control system 8 controls the air injection pump 9 to inject air into the electrode 22 pressure chamber 19 according to the set standard pressure, and pushes the electrode 22 out of the puncture guide needle 1 to enter the tumor. After reaching the set position, the AI control system 8 controls to close the rear air injection tube 21, maintains the pressure in the electrode 22 pressure chamber 19, and locks the position of the electrode 22. High voltage nanosecond pulses are introduced from the electrode 22 crimping socket 7 for tumor ablation. According to the ablation operation scheme, if several times of pulse ablation are needed, the AI control system 8 controls to turn on the rear emptying switch 20, and makes the rear sealing piston 6 return to the initial position (the electrode 22 return to the track of the puncture guide needle 1) through spring force. The puncture guide needle 1 can adjust the outlet direction of the electrode 22 in situ by adjusting the puncture needle tube seat 3 to rotate 180 degrees or any preset angle, then the rear emptying switch 20 is turned off, air is injected into the electrode 22 pressure chamber 19 again to push the electrode 22 out of the puncture guide needle 1 to enter the tumor. By repeating the operations for many times, the coverage range of the electric field can be increased and the treatment effect of pulse ablation can be improved.

After the treatment through nanosecond pulse ablation, the front emptying switch 18 and the rear emptying switch 20 are turned on to make the front sealing piston 5 and the rear sealing piston 6 return to the initial positions, and to retract the puncture guide needle 1 and the electrode 22.

Figure 4:
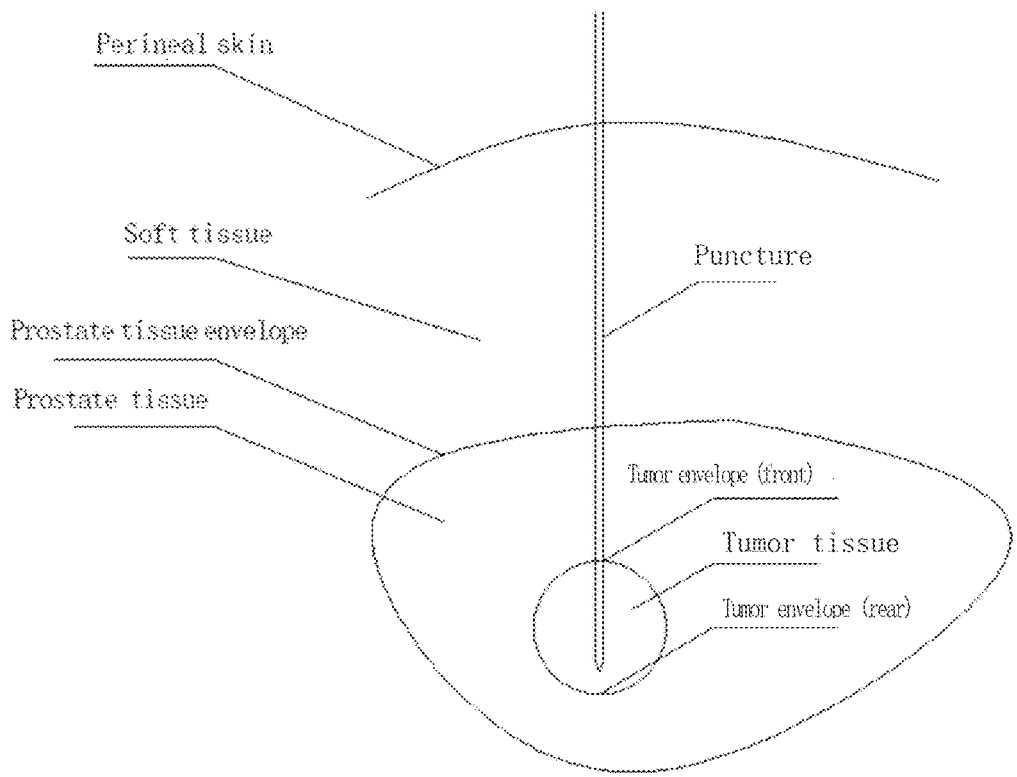
FIG. 4 illustrates a schematic view of puncture according to the present application.
Figure 5:
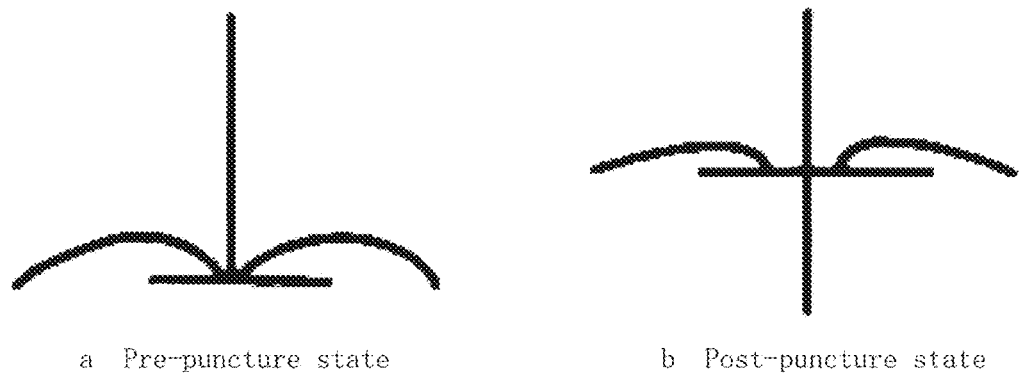
FIG. 5 illustrates a schematic view before and after puncture according to the present application.
Figure 6:
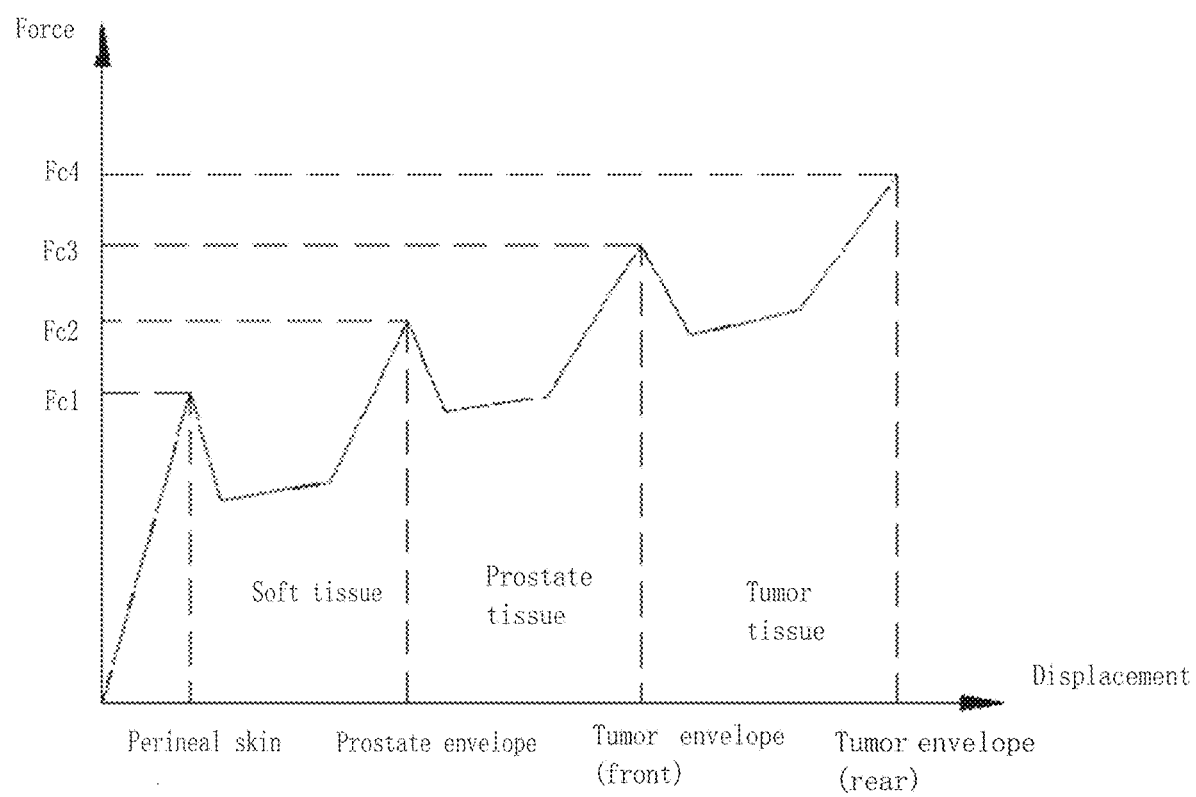
FIG. 6 illustrates a change chart of puncture force of different tissues.
Figure 7:
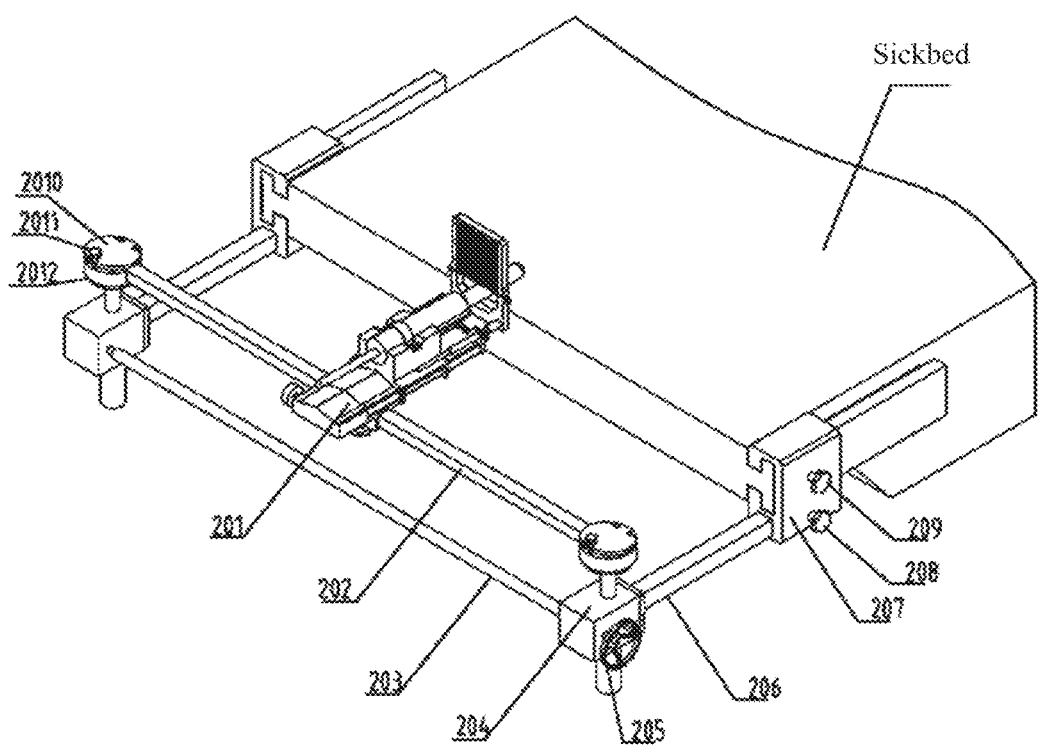
FIG. 7 illustrates a structural schematic view of a positioning system according to the present application.
Figure 8:
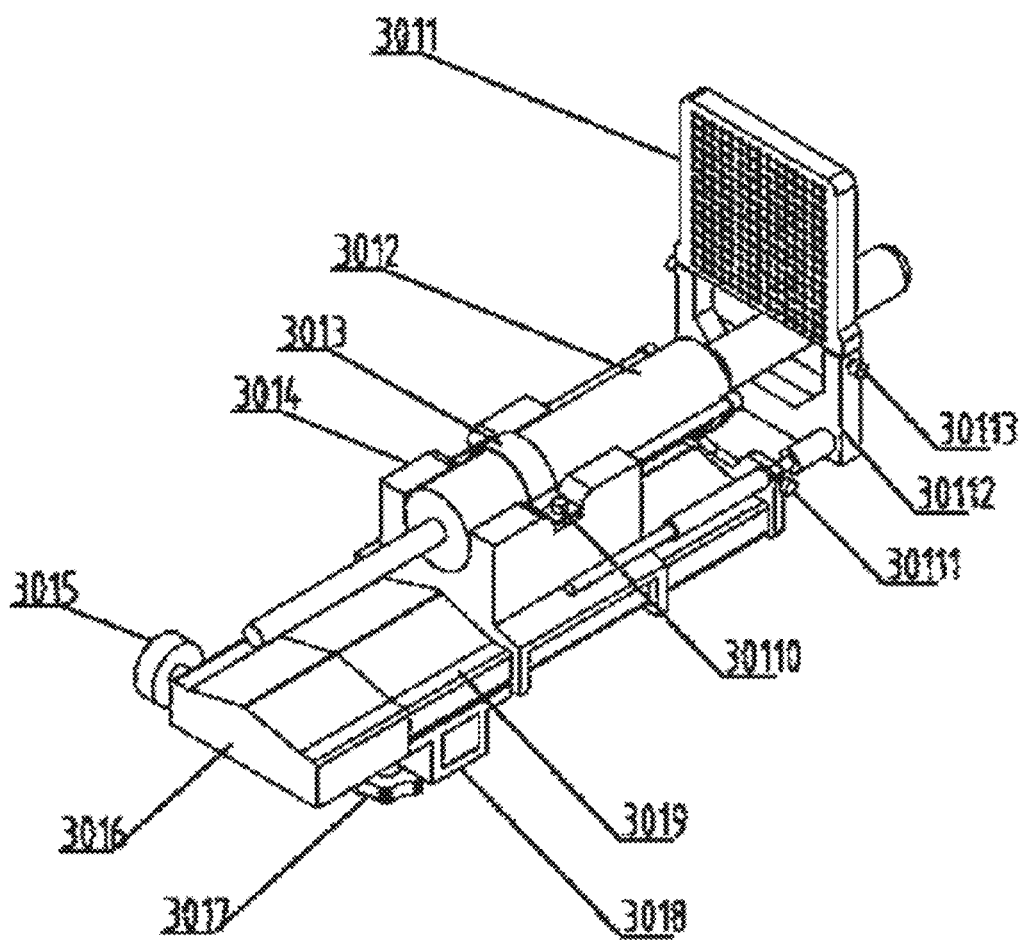
FIG. 8 illustrates a structural schematic view of an orientation device according to the present application.
Figure 9:
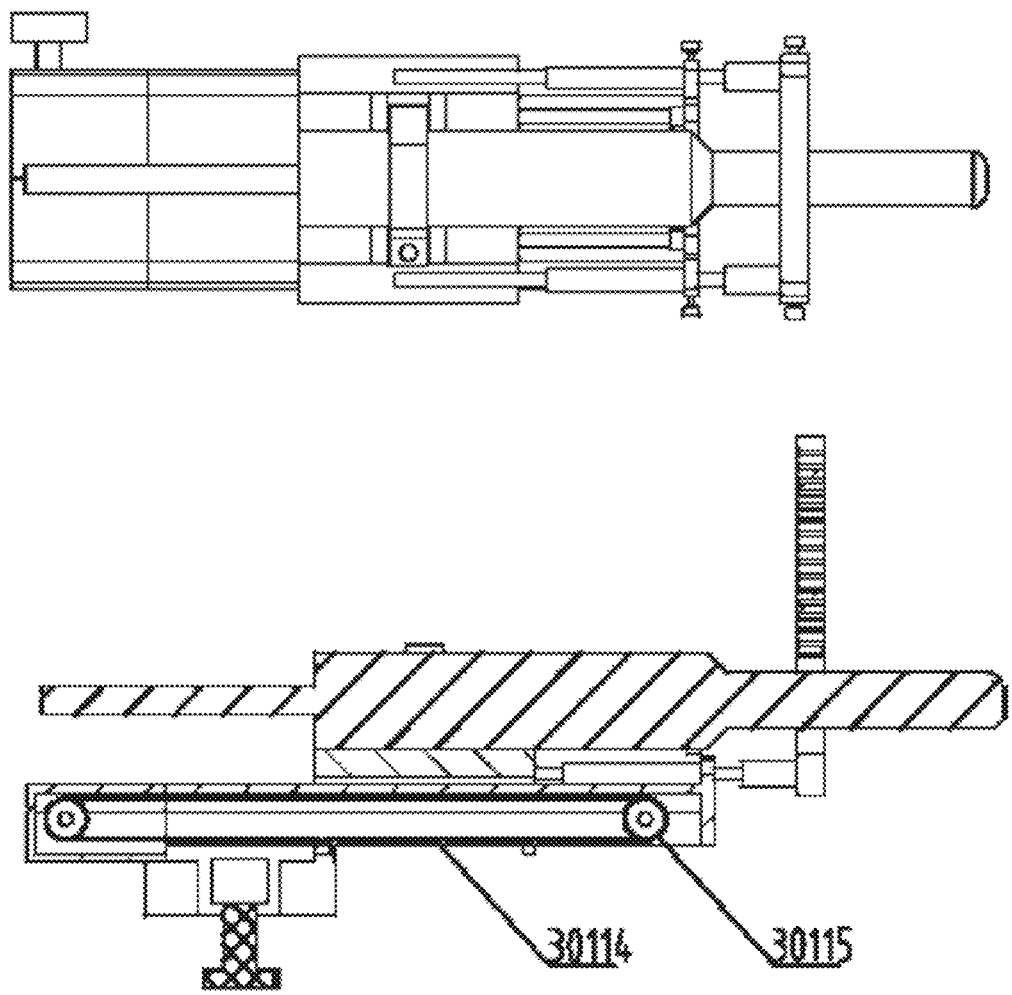
FIG. 9 illustrates a sectional view of an orientation device according to the present application.
Figure 10:
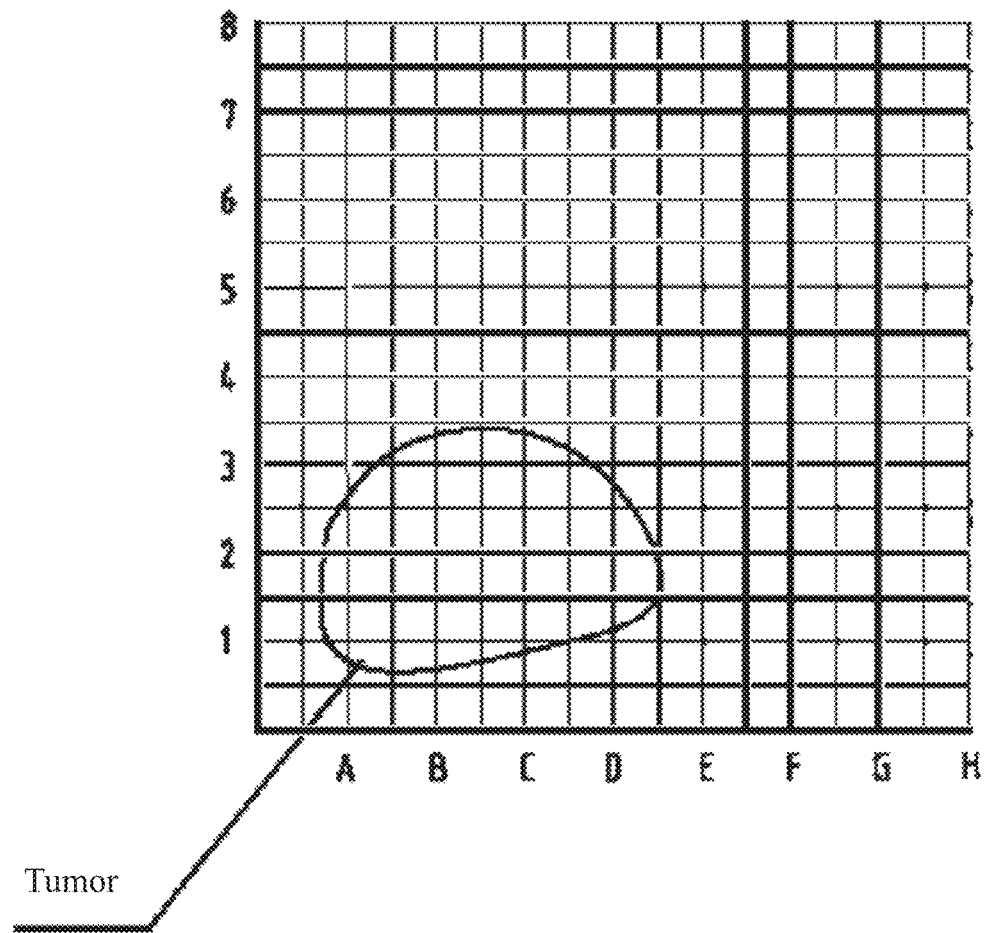
FIG. 10 illustrates a schematic view of tumor orientation according to the present application.

Referring to FIGS. 4-6, a specific embodiment of arranging the sensor module of the present application is as follows:

The change of the puncture force in different tissue layers is due to the difference in characteristic density, viscoelasticity, tension and pressure resistance of tissues. At present, the widely used tissue characteristic detection technologies in clinic may be divided into contact type and non-contact type. Contact type instruments, such as skin compression elastometer, generally reflect the static elastic characteristics of tissues. Non-contact instruments, such as ultrasound, MM and other imaging technologies, benefit from the development of ultrasound imaging technology. The existing technology can extract tissue elasticity information from ultrasonic scattering echoes, and Doppler velocity measurement and cross-correlation technologies are used to reflect the dynamic elastic characteristics of tissues.

DICOM3.0 standard is the only standard for image communication and exchange of international medical imaging equipment. An AI integrated medical image management system based on this standard can easily connect ultrasound and other equipment to realize real-time image acquisition and post-processing. The AI system makes the surgical treatment scheme according to the collected parameters of tissues through which the puncture needle passes.

Taking the treatment of a prostate tumor as an example, in order to enter the tumor, the puncture needle needs to pass through perineal skin, soft tissues, prostate tissue envelope, prostate tissues, tumor envelope and tumor tissues. The process of needle puncture is divided into a pre-puncture stage and a post-puncture stage. In the pre-puncture stage, the puncture force of the needle is equal to the resistance encountered thereby. In the post-puncture stage, the puncture force is composed of friction force and cutting force. In the pre-puncture state, the force on the needle tip increases steadily until it suddenly decreases, indicating that it enters the puncture state.

In the process of needle puncture, when the puncture force reaches a first critical value Fc1, there will be a sharp drop, indicating that the needle pierces the perineal skin and enters the soft tissues. When it reaches Fc2, it begins to enter a second layer of tissues, and so on. When the puncture needle punctures the perineal skin, the AI system collects the pressure value detected by the pressure sensor 12. After puncturing the skin, the resistance decreases and it is determined the puncture needle has entered the soft tissue region. The numerical value of the puncture depth sensor 11 is collected to determine the depth of the puncture needle into the soft tissues. As above, the AI system can determine which tissue and depth the puncture needle punctures section by section, compare with the operation scheme to determine whether the puncture is correct in real time, and give an early warning: if the pressure range or puncture depth range is exceeded, the color of the lamp in the normal state changes to flashing or highlighting, and the puncture is stopped to remind a doctor to check the type-B ultrasound images to determine to continue the puncture or exit and start again.

Referring to FIGS. 7-10, a specific embodiment of the positioning system of the present application is as follows:

Through the orientation control system 8, the type-B ultrasound probe is controlled to enter the human body from the anus, and the lesion region is found through the ultrasound image. The AI system reads the ultrasound image, establishes grid lines with the center of the type-B ultrasound probe, positions the tumor tissues, adjusts the position of the type-B ultrasound probe to make the tumor all in the grid lines, and locks the position of the probe. The AI system makes the operation scheme based on the electric field pulse database and image data, and determines the position of the tumor that the electrode 22 needs to enter on the grid. At the front end of the probe, an orientation plate 3011 with the same scale to the grid lines of the AI system is provided, and the treatment electrode 22 punctures the tumor according to the surgical scheme selected by the doctor for high-voltage nanosecond pulse ablation.

The positioning system consists of an orientation device 201, a transverse support rod 202, a lifting connecting rod 203, lifting platforms 204, a lifting rocker 205, a longitudinal support rod 206, a fixed locking block 207, a longitudinal rod locking handle 208, a fixing frame locking handle 209, a lifting pressing block 2010, a lifting locking handle 2011, and a lifting fixing block 2012.

The orientation device 201 includes an orientation plate 3011, an ultrasonic probe 3012, a probe fixing strip 3013, a probe fixing frame 3014, a probe adjusting handle 3015, a positioning frame rear plate 3016, a positioning frame locking handle 3017, a positioning frame fixing plate 3018, a positioning frame 3019, a probe locking screw 30110, an orientation plate frame locking screw 30111, an orientation plate fixing frame 30112, an orientation plate locking screw 30113, a synchronous belt pulley I 30114 and a synchronous belt pulley II 30115.

A specific embodiment of the positioning system of the present application is as follows: the fixed locking block 207 sleeves a sickbed guide groove and the position is locked through the longitudinal rod locking handle 208; the longitudinal support rod 206 is mounted on the fixed locking block 207, the position is locked through the fixing frame locking handle 209, and the distance is capable of being roughly adjusted according to the position of a human body; the lifting platforms 204 are fixed on the longitudinal support rod 206, the lifting connecting rod 203 between the two lifting platforms 204 is connected to make the lifting synchronous, and the lifting rocker 205 is mounted on the lifting platform 204 on one side; the lifting fixing block 2012 is provided on the lifting platform 204, the transverse support rod 202 is disposed in a lifting fixing block 2012 clamping slot, a hinge structure is provided between the lifting pressing block 2010 and the lifting fixing block 2012, and the lifting locking handle 2011 fixedly locks the transverse support rod 202; the orientation device 201 is fixed on the transverse support rod 202 through a clamping slot in the positioning frame fixing plate 3018, and the position is capable of being adjusted on the left and right of the transverse support rod 202 and is capable of being locked through the positioning frame locking handle 3017; after the patient is in place on the sickbed, the height of the lifting platforms 204 is adjusted through the lifting rocker 205, and the left and right positions of the orientation device 201 are adjusted through the positioning frame fixing plate 3018, such that the ultrasonic probe 3012 is aligned with the patient's anus; the positioning frame 3019 is provided on the positioning frame fixing plate 3018, the probe fixing frame 3014 is provided at an upper end of the positioning frame 3019, the ultrasonic probe 3012 is fixed in a groove in the probe fixing frame 3014, and the position is locked through the probe locking screw 30110 through the probe fixing strip 3013; the orientation plate fixing frame 30112 is provided at a front end of the positioning frame 3019, and the position is locked through the orientation plate frame locking screw 30111; the orientation plate 3011 is provided on the orientation plate fixing frame 30112, and the position is locked through the orientation plate locking screw 30113; the inside of the positioning frame 3019 is hollow and is provided with the synchronous belt pulley I 30114 and the synchronous belt pulley II 30115, the probe fixing frame 3014 is fixed on the synchronous belt pulley I 30114, the positioning frame rear plate 3016 is provided at a rear end of the positioning frame 3019, the probe adjusting handle 3015 is provided on the positioning frame rear plate 3016, the probe adjusting handle 3015 is fixed coaxially with the synchronous belt pulley II 30115, and the ultrasonic probe 3012 is capable of moving forward or backward through the probe adjusting handle 3015.

Figure 11:
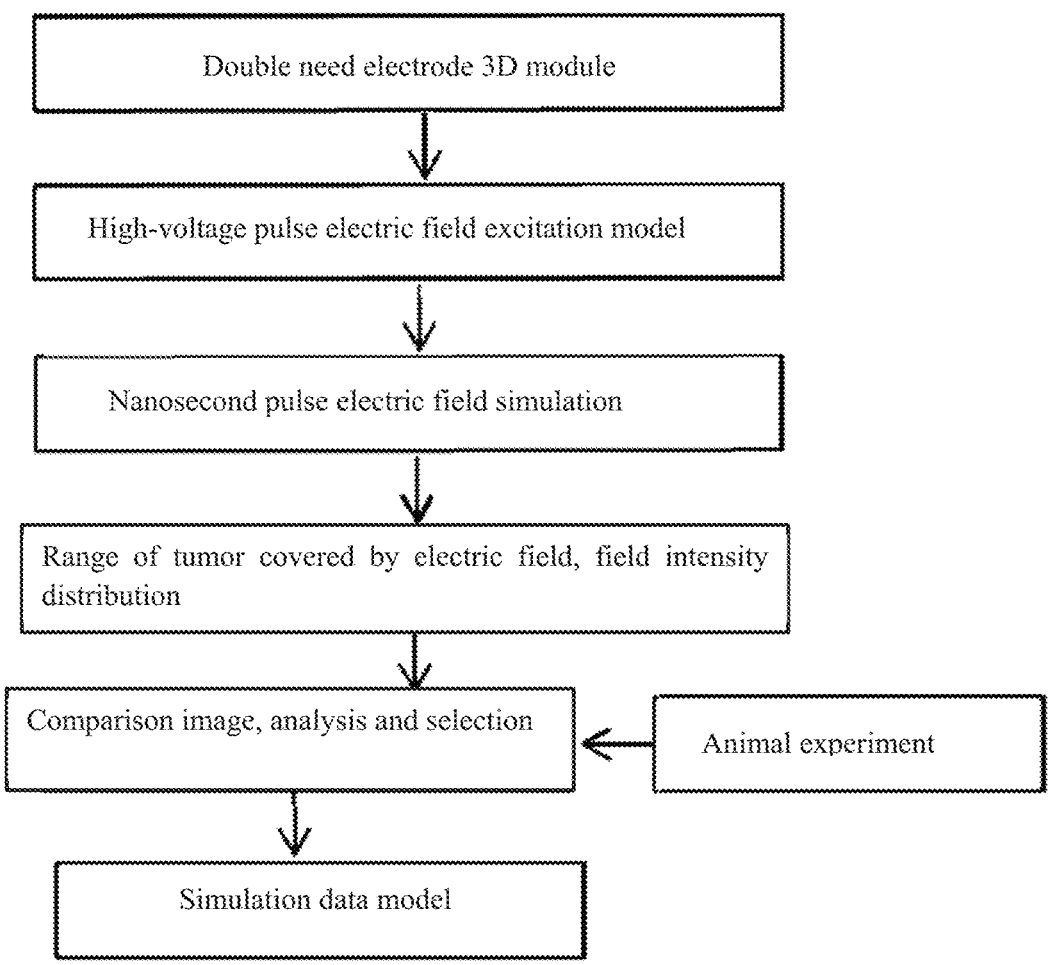
FIG. 11 illustrates a flowchart of a simulation method according to the present application.
Figure 12:
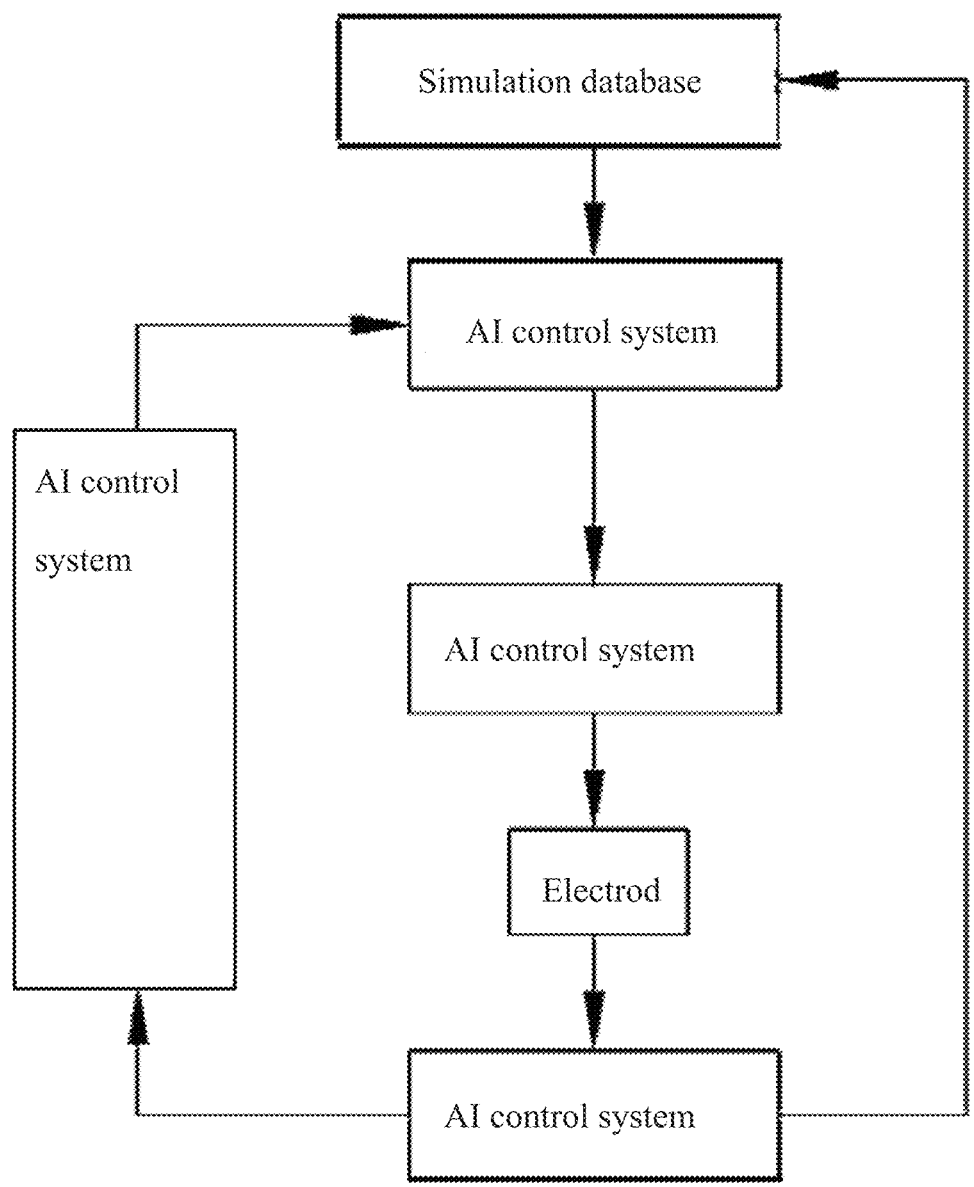
FIG. 12 illustrates a flowchart of adaptation of pulse parameters according to the present application.

Referring to FIGS. 11-12, a simulation method applicable to an electric pulse ablation device includes: establishing a simulation database, which specifically includes the following steps:
step 1: collecting tumor image data, establishing a database, and marking accurate regions of tumors in tissues;
step 2: according to the tissue parameters, the spacing between different double needle electrodes and the length of an electrode working part, establishing a parameter 3D model;
step 3: realizing the variation of the spacing and the length through the parameter 3D model, simulating different pulse amplitudes, pulse widths, pulse frequencies and feed modes, performing simulation based on different parameter 3D models, and selecting and adding parameter settings with large electric field coverage range and uniform field intensity distribution into the simulation database.
step 5: analyzing a solid tumor and giving setting schemes: taking ultrasonic images of a patient, performing analysis to form a tumor tissue 3D model, selecting suitable application data in the simulation database, and simulating the placement of a single group or a plurality of groups of electrodes according to the size and morphology of the tumor to form varied pulse setting schemes as setting bases for selection by doctors. The time of the doctors is saved, and the reasonableness and effectiveness of parameter settings are improved.

The present application can, by establishing a simulation database, perform simulation according to tumors to obtain parameter setting values of the ablation device as setting bases for selection by doctors, can effectively decrease the burden of the doctors, and is time-saving and labor-saving. In addition, the parameters set at each time are not influenced by the external world, and thus the reasonableness and effectiveness of the parameter settings are effectively kept.

A specific embodiment of the present application is as follows:
in step 1, a full-automatic segmentation model of tissues and tumors is designed by using a convolutional neural network based on a DenseNet network model; then learning is performed by using marked original images in the database and a tumor mask of the same group as inputs of a convolutional network;
in step 2, the tissue parameters are tissue dielectric constant, relative permeability, bulk conductivity and dielectric loss tangent.

Figure 13:
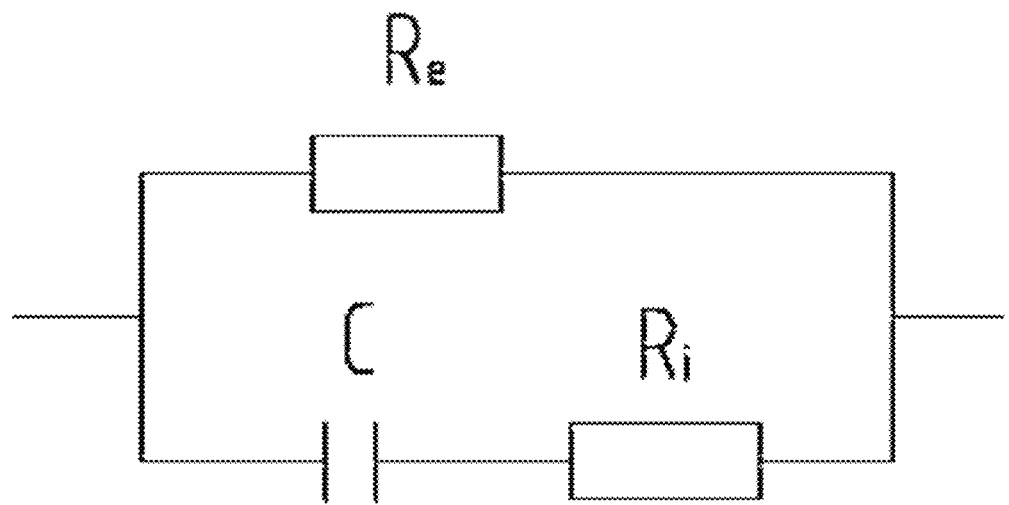
FIG. 13 illustrates a three-element equivalent circuit of tissues according to the present application.

A specific embodiment of a conductivity change process, i.e., impedance adaption process in the ablation process of the present application is as follows:
A change model of the tissue conductivity and the external ablation electric field is established, and the intensity of the external ablation electric field is calculated according to the change of the tissue conductivity;
a functional relationship between the tissue conductivity and the external ablation electric field is as follow:

$$\sigma=\sigma_0(1+\alpha(T-T_0))+(\sigma'-\sigma_0)F_{flc}(E-E_1,E_{range})$$

where $T=T_0$ all the time since the temperature of a pulse electric field does not change or changes very slightly;
$\sigma_0$ is the initial conductivity of tissues, and the initial conductivity of normal tissues and tumors are capable of being measured through a test circuit;
$\sigma'$ is the conductivity of tissues only in an electric field, and the conductivity of normal tissues and tumors is capable of being measured through a test circuit;
$F_{flc}$ is a smooth Heaviside function with second-order continuous derivatives;
E is the intensity of the electric field;
the values of $E_1$ and $E_{range}$ are respectively 30 KV/cm−X and 30 kV/cm+X, where X is a voltage threshold, so as to ensure that the conductivity changes with the intensity of the electric field within a range of the intensity threshold of the electric field forming functional changes in cells;
$\alpha$ is a calculation coefficient;
in the process of electric pulse ablation, the impedance of the tumor tissues and the electrolyte parameters of the tissue seeping fluid in the ablation region change with the ablation time, and the changing electrolyte parameters are not matched with the initial electric pulse ablation parameters anymore, resulting in that the ablation effect is poor; therefore, in order to ensure that the reasonable pulse parameters can be set and the change of electrolyte parameters can be understood in real time, the input pulse parameters are adjusted in time to keep adaptive high voltage and steep pulse to achieve the best tumor destruction effect;
the conductivity and the impedance Z are mutually reciprocals;

referring to FIG. 13, the tissue impedance change calculation formula is as follow: $Z=R_e//(Z_C+R_i)$ where $Z_C=1/(2\pi fC)$, where $R_i$, $R_e$ and C are respectively equivalent to intracellular fluid resistance, extracellular fluid resistance and cell membrane capacitance, and f represents current frequency. According to the initial impedance of the tissues, the initial conductivity of the tissues can be calculated, so as to facilitate formula application.

Figure 14:
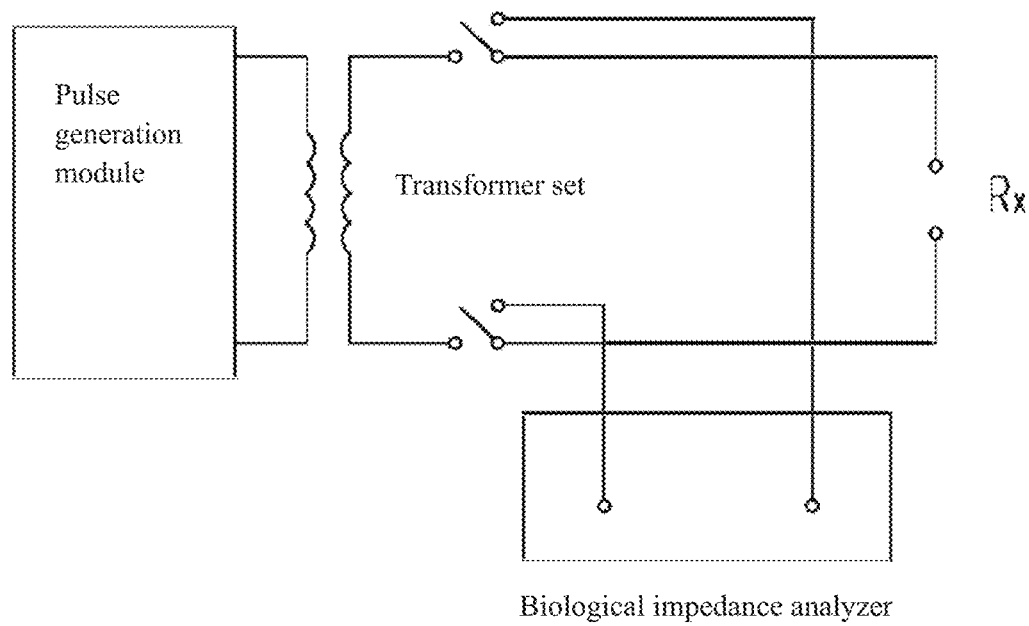
FIG. 14 illustrates a circuit diagram of an impedance test system according to the present application.

By using the electric pulse parameters obtained through simulation as the initial electric pulse parameters of the pulse generator, the tumor is ablated. In the process of ablation, the impedance of the tumor tissues changes with the ablation time. In the process of ablation, the pulse current intensity is monitored in real time. When the current value reaches a certain value/variable, the system automatically switches the impedance detection circuit. The impedance detection circuit is as illustrated in FIG. 14. The impedance is measured through the impedance detection circuit to obtain the impedance value. Through high-speed USB, Ethernet or WLAN connection, the data are transmitted to the AI control system, and then the data are processed, and the pulse generator is instructed to automatically match the electric pulse parameters.

Figure 15:
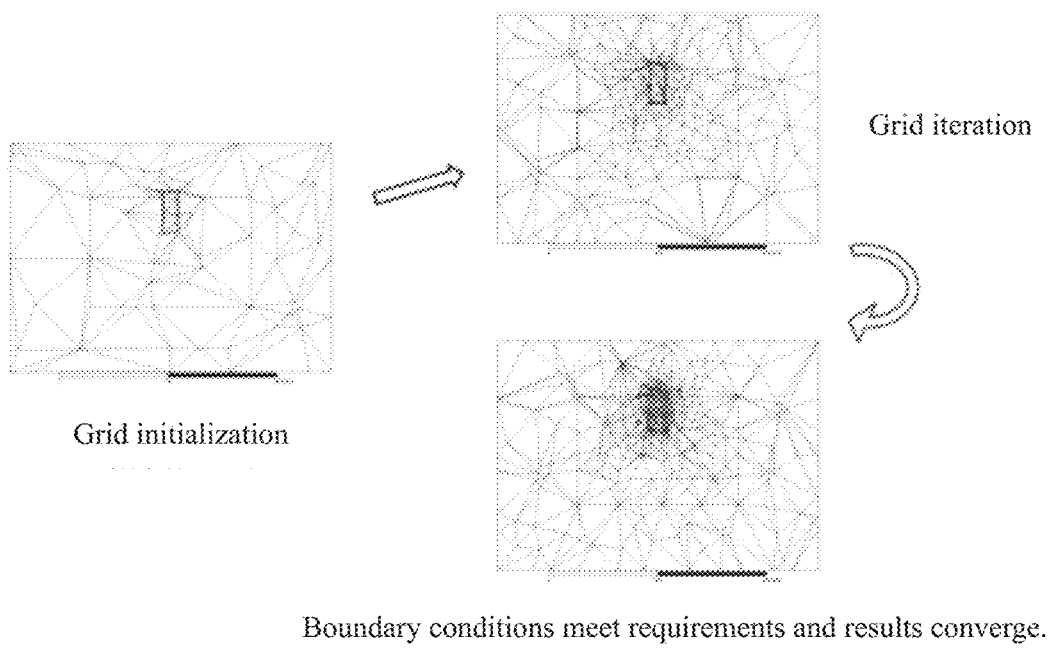
FIG. 15 illustrates a schematic diagram of grid computation adopted in the present application.

A specific embodiment of the computation of the electric field of the present application during initial modeling is as follows:

a finite-element simulation algorithm based on a discontinuous Galerkin time domain algorithm is used to establish the model, and the electric field distribution in tumors and normal tissues is obtained by solving the following equation:

$$\nabla \times \left(\frac{1}{\mu_r}\nabla \times E\right) - k_o^2 \epsilon_r E = 0$$

where $\mu_r$ is the relative permeability of a medium; $\epsilon_r$ is the relative conductivity of the medium; k is Coulomb constant; E is the intensity of the electric field; through the above formula, the intensity of the electric field of the tissues under a normal state can be obtained, so as to determine more reasonable initial pulse parameters;

referring to FIG. 15, in order to obtain the optimal pulse parameters and electrode placement for different shapes and sizes of tumors, a grid initialization algorithm and an optimized iterative adaptation algorithm are used to optimize the pulse parameters and electrode parameters; grids are coupled by numerical flux and are automatically refined and subdivided, convergence is achieved after several iterations, and the electric field distribution in the solution region meets characteristics of a physical environment and boundary conditions.

What are described above are just exemplary embodiments of the present application and are not intended to limit the present application. Any modification, equivalent replacement and improvement made within the spirit and principle of the present application should be included in the scope of protection the present application.

The invention claimed is:

1. An electric pulse ablation device, wherein the electric pulse ablation device comprises a pulse generator, a positioning system, a needle feeding mechanism, a sensor module, a biological impedance analyzer, and an impedance adaptation system, wherein the pulse generator is configured to generate an electric pulse;

the positioning system is configured to read the size and position of tissues;

the needle feeding mechanism is provided with a puncture guide needle;

the sensor module is configured to sensor puncture pressure;

the biological impedance analyzer is configured to monitor the impedance of tissues in real time;

the impedance adaptation system is configured to adjust pulse parameters of the pulse generated by the pulse generator, wherein the needle feeding mechanism comprises a base, a puncture needle tube seat, a support frame, a front sealing piston, a rear sealing piston, an electrode crimping socket, an air injection pump, an indicator lamp, a pin tumbler lock, a front air vent, a rear air vent, a puncture needle pressure chamber, a front air injection tube, a front emptying switch, an electrode pressure chamber, a rear emptying switch, a rear air injection tube, and an electrode.

2. The electric pulse ablation device according to claim 1, wherein the positioning system comprises an orientation device, a transverse support rod, a lifting connecting rod, lifting platforms, a lifting rocker, a longitudinal support rod, a fixed locking block, a longitudinal rod locking handle, a fixing frame locking handle, a lifting pressing block, a lifting locking handle, and a lifting fixing block;

the fixed locking block is configured to sleeve a sickbed guide groove and the longitudinal rod locking handle is configured to lock the position;

the longitudinal support rod is mounted on the fixed locking block, the position is locked through the fixing frame locking handle, and the distance is capable of being roughly adjusted according to the position of a human body; the lifting platforms are fixed on the longitudinal support rod, the lifting connecting rod between the two lifting platforms is connected to make the lifting synchronous, and the lifting rocker is mounted on the lifting platform on one side; the lifting fixing block is provided on the lifting platform, the transverse support rod is disposed in a lifting fixing block clamping slot, a hinge structure is provided between the lifting pressing block and the lifting fixing block, and the lifting locking handle fixedly locks the transverse support rod.

3. The electric pulse ablation device according to claim 2, wherein the orientation device comprises an orientation plate, an ultrasonic probe, a probe fixing strip, a probe fixing frame, a probe adjusting handle, a positioning frame rear plate, a positioning frame locking handle, a positioning frame fixing plate, a positioning frame, a probe locking screw, an orientation plate frame locking screw, an orientation plate fixing frame, an orientation plate locking screw, a synchronous belt pulley I and a synchronous belt pulley II;

the orientation device is fixed on the transverse support rod through a clamping slot in the positioning frame fixing plate, and the position is capable of being adjusted on the left and right of the transverse support rod and is capable of being locked through the positioning frame locking handle; the positioning frame is provided on the positioning frame fixing plate, the probe fixing frame is provided at an upper end of the positioning frame, the ultrasonic probe is fixed in a groove in the probe fixing frame, and the position is locked through the probe locking screw through the probe fixing strip; the orientation plate fixing frame is provided at a front end of the positioning frame, and the position is locked through the orientation plate frame locking screw; the orientation plate is provided on the orientation plate fixing frame, and the position is locked through the orientation plate locking screw; the inside of the positioning frame is hollow and is provided with the synchronous belt pulley I and the synchronous belt pulley II, the probe fixing frame is fixed on the synchronous belt pulley I, the positioning frame rear plate is provided at a rear end of the positioning frame, the probe adjusting handle is provided on the positioning frame rear plate, the probe adjusting handle is fixed coaxially with the synchronous belt pulley II, and the ultrasonic probe is capable of moving forward or backward through the probe adjusting handle.

4. The electric pulse ablation device according to claim 1, wherein the sensor module comprises a pressure sensor module and a depth sensor.

\* \* \* \* \*